(12) United States Patent
Carney et al.

(10) Patent No.: US 10,307,303 B2
(45) Date of Patent: Jun. 4, 2019

(54) WEARABLE ABSORBENT ARTICLE

(71) Applicant: SCA Hygiene Products AB, Göteborg (SE)

(72) Inventors: Joshua Daniel Carney, Göteborg (SE); Yossef Schvetz, Milan (IT); Serdar Ozsumer, Milan (IT); Manuel Tramontana, Milan (IT); Alessandro Locati, Milan (IT)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 16/064,615

(22) PCT Filed: Dec. 22, 2015

(86) PCT No.: PCT/EP2015/081036
§ 371 (c)(1),
(2) Date: Jun. 21, 2018

(87) PCT Pub. No.: WO2017/108109
PCT Pub. Date: Jun. 29, 2017

(65) Prior Publication Data
US 2018/0369025 A1 Dec. 27, 2018

(51) Int. Cl.
*A61F 13/42* (2006.01)
*A61F 13/84* (2006.01)
*A61F 5/48* (2006.01)

(52) U.S. Cl.
CPC ............... *A61F 13/42* (2013.01); *A61F 5/48* (2013.01); *A61F 2013/424* (2013.01); *A61F 2013/8476* (2013.01); *A61F 2013/8479* (2013.01)

(58) Field of Classification Search
CPC .... A61F 13/42; A61F 2013/8479; A61F 5/48; G01N 27/121; G01N 27/07; G01N 27/048
See application file for complete search history.

(56) References Cited

U.S. PATENT DOCUMENTS

| 4,356,818 A | * | 11/1982 | Macias | A61F 13/42 128/886 |
| 5,266,928 A | * | 11/1993 | Johnson | A61F 13/42 128/886 |
| 5,469,145 A | * | 11/1995 | Johnson | A61F 5/48 128/886 |

(Continued)

FOREIGN PATENT DOCUMENTS

| WO | WO-2012/084987 A2 | 6/2012 |
| WO | WO-2014/035340 A1 | 3/2014 |
| WO | WO-2015/068124 A1 | 5/2015 |

*Primary Examiner* — Hoi C Lau
(74) *Attorney, Agent, or Firm* — Drinker Biddle & Reath LLP (57) ABSTRACT

A wearable absorbent article includes a conductor arrangement. Including a plurality of elongate conductors, each conductor extending along an extension direction. At least some of the conductors have different lengths from each other in the respective extension directions. Those of the at least some of the conductors which have larger lengths in the respective extension directions have lower electrical resistances per unit length than those of the at least some of the conductors which have smaller lengths in the respective extension directions.

13 Claims, 6 Drawing Sheets

(56) References Cited

U.S. PATENT DOCUMENTS

| | | | | |
|---|---|---|---|---|
| 5,659,294 A * | 8/1997 | Schroder | ............... | B60S 1/0822 |
| | | | | 200/61.05 |
| 5,838,240 A * | 11/1998 | Johnson | .................... | A61F 5/48 |
| | | | | 340/604 |
| 6,097,297 A * | 8/2000 | Fard | ........................ | A61F 13/42 |
| | | | | 128/886 |
| 7,250,547 B1 * | 7/2007 | Hofmeister | ............. | A61F 13/42 |
| | | | | 340/573.5 |
| 9,408,757 B2 * | 8/2016 | Elfstrom | ................. | A61F 13/42 |
| 9,719,951 B1 * | 8/2017 | Woodbury | ........... | G01N 27/048 |
| 9,910,003 B1 * | 3/2018 | Lastinger | ............. | G01N 27/121 |
| 10,111,787 B2 * | 10/2018 | Ying | ................ | A61F 13/15707 |
| 10,191,003 B1 * | 1/2019 | Lastinger | ............. | G01N 27/121 |
| 2008/0051745 A1 * | 2/2008 | Long | ....................... | A61F 13/42 |
| | | | | 604/361 |
| 2008/0058744 A1 * | 3/2008 | Tippey | .................... | A61F 13/42 |
| | | | | 604/361 |
| 2008/0266123 A1 * | 10/2008 | Ales | ........................ | A61F 13/42 |
| | | | | 340/604 |
| 2013/0307570 A1 * | 11/2013 | Bosaeus | ................ | G01N 27/07 |
| | | | | 324/694 |
| 2015/0042489 A1 * | 2/2015 | LaVon | .................... | A61F 13/42 |
| | | | | 340/870.11 |
| 2016/0051417 A1 * | 2/2016 | Chiu | ....................... | A61F 13/42 |
| | | | | 604/361 |
| 2017/0354374 A1 * | 12/2017 | Pepin | .................. | A61B 5/0002 |
| 2017/0354546 A1 * | 12/2017 | Krasnow | ................ | A61F 13/42 |
| 2018/0369025 A1 * | 12/2018 | Carney | ................... | A61F 13/42 |

* cited by examiner

WEARABLE ABSORBENT ARTICLE

CROSS-REFERENCE TO PRIOR APPLICATION

This application is a § 371 National Stage Application of PCT International Application No. PCT/EP2015/081036 filed Dec. 22, 2015, which is incorporated herein in its entirety.

TECHNICAL FIELD

The present disclosure relates to a wearable absorbent article, such as a diaper, a sanitary towel, an incontinence garment or a medical dressing, including a conductor arrangement.

TECHNICAL BACKGROUND

Wearable absorbent articles, such as diapers, sanitary towels, incontinence garments, medical dressings and the like, have wide-spread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption which, if exceeded, will cause the absorbent article to become ineffective, e.g., to leak, or at least to fail to absorb further.

Therefore, users of such articles, or their carers, must predict when an absorbent article is nearing its absorbent capacity and must then take steps to replace the article before capacity is reached. In situations where there are many users of such absorbent articles with relatively fewer carers, such as in institutional settings, the management of the capacity of the various absorbent articles in use becomes a significant administrative burden.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established and appropriate absorbent articles may be provided.

Systems which are able to alert the user or carer to saturation or impending saturation of the absorbent article are therefore of benefit. Such systems may take the form of wetness sensors for detecting wetness within the absorbent article. The wetness sensors may use a conductor arrangement provided in the wearable absorbent article for detecting wetness by measuring the resistance between different conductors of the conductor arrangement. In this way, wetness sensors can be capable of determining both the amount of wetness and the location where the wetness event has occurred in the absorbent article.

One approach to an absorbent article containing a wetness sensor is described in WO 2012/084987.

However, when using such wetness sensors and conductor arrangements for wetness detection, the resistances of the conductors may significantly contribute to the measured resistance, especially when conductors of relatively small cross-sectional area are desired. Hence, the accuracy of the measurement, in terms of both the wetness amount and the location of the wetness event, is considerably reduced, in particular, for the case of conductors with different lengths from each other.

Hence, there remains a need for a wearable absorbent article that allows for the detection of wetness at one or more locations within the absorbent article, in particular, at one or more locations within an absorbent core of the absorbent article, with a high degree of accuracy.

SUMMARY

Accordingly, it is desired to provide a wearable absorbent article that allows for wetness at one or more locations within the absorbent article, in particular, at one or more locations within an absorbent core of the absorbent article, to be detected with a high degree of accuracy.

The disclosure provides a wearable absorbent article, such as a wearable absorbent hygiene article, including a conductor arrangement, wherein the conductor arrangement includes a plurality of elongate conductors, each conductor extending along an extension direction. At least some of the conductors have different lengths from each other in the respective extension directions. Those of the at least some of the conductors which have larger lengths in the respective extension directions have lower electrical resistances per unit length than those of the at least some of the conductors which have smaller lengths in the respective extension directions.

Throughout this disclosure, the term "wearable absorbent article" is to be interpreted as any article that can be worn by a user and which may absorb certain substances expelled by the user, especially urine. Wearable absorbent articles include, for example, pull-on diapers, refastenable diapers, reusable diapers and other types of diapers as well as absorbent pads and/or absorbent inserts that are intended to be placed in the underwear. Further, the wearable absorbent article may be a sanitary towel, an incontinence garment, a medical dressing or the like.

For example, the wearable absorbent article may include a liquid permeable inner layer or top layer adapted to face the wearer during use and adapted to allow a fluid, such as urine or other bodily fluids, to pass through, a liquid impermeable outer layer or bottom layer adapted to face away from the wearer and adapted to prevent the fluid from passing through, and an absorbent core located between the inner or top layer and the outer or bottom layer to absorb the fluid.

The electrical resistance per unit length may be defined at a conductor temperature of 20° C.

The conductor arrangement may include two or more conductors, three or more conductors, four or more conductors, five or more conductors, or six or more conductors.

As used herein, the term "substantially" encompasses deviations within the measuring tolerance. In some embodiments, the term "substantially" may encompass deviations within ±10%, within ±5%, within ±3% or within ±1%.

As used herein, the term "extension direction" defines the direction along which a particular conductor extends, i.e., the direction along the length of the particular conductor. The extension direction may be a straight direction but is not restricted thereto. For example, alternatively, the extension direction may be a curved or curvilinear direction, an undulating or wavy direction, an elliptic or circular direction etc.

At least some of the conductors of the conductor arrangement have different lengths from each other in the respective extension directions. In embodiments, the conductor arrangement of the wearable absorbent article can thus allow for wetness to be detected at different locations within the absorbent article which are spaced apart from each other, enabling detection of the location or locations where the wetness event or events has or have occurred.

The conductors of the conductor arrangement are electrical conductors. The electrical resistance of an electrical conductor is proportional to its length. Hence, electrical conductors with larger lengths have higher electrical resistances than electrical conductors with smaller lengths, if the remaining parameters of the conductors, such as cross-sectional area and material, are the same. For the case of conventional conductor arrangements, when detecting wetness in an absorbent article by measuring the resistances between conductors of different lengths, the differences in resistance resulting from these different lengths will affect the resistance measurement, considerably reducing the measurement accuracy in terms of both the wetness amount and the location of the wetness event.

In an embodiment, the conductor arrangement of the absorbent article, those of the at least some of the conductors which have larger lengths in the respective extension directions have lower electrical resistances per unit length than those of the at least some of the conductors which have smaller lengths in the respective extension directions. Hence, the differences in resistance, i.e., overall or total resistance, of the conductors resulting from their different lengths can be reduced or even eliminated. The absorbent article thus allows for wetness at one or more locations within the absorbent article to be detected with a high degree of accuracy.

The wearable absorbent article may further include an absorbent core. Moreover, the wearable absorbent article may include a wetness detection unit for detecting wetness at one or more locations within the absorbent core, wherein the conductors are arranged so as to be electrically insulated from the absorbent core.

The wetness detection unit may be any type of detection unit capable of detecting wetness at one or more locations within the absorbent core by measuring an electrical resistance or electrical resistances through the conductors.

Since the conductors are arranged so as to be electrically insulated from the absorbent core, any short circuits between the conductors, for example, in the case of a wetness event, are reliably prevented. In this way, a particularly high measurement accuracy can be ensured.

Each of the conductors of the conductor arrangement may be electrically connected to a respective electrode. In this case, the wearable absorbent article includes a plurality of electrodes, wherein each of the electrodes is in electrical connection with a respective conductor of the conductor arrangement.

Each of the electrodes may be electrically connected to a respective conductor at the distal end of the conductor in the extension direction thereof, i.e., the end of the conductor which is disposed further away from the wetness detection unit.

The electrodes may be arranged in contact with the absorbent core. In this way, upon the occurrence of a wetness event in the absorbent core, an electrical contact is established between a respective one or respective ones of the electrodes and the absorbent core, and an electrical contact is established between a pair of electrodes through the absorbent core.

The conductor arrangement may include an insulating substrate and an insulating layer arranged on top of the substrate. The insulating layer may cover the conductors while exposing the electrodes. For example, the insulating layer may have one or more openings, such that the conductors are covered by the insulating layer and the electrodes are exposed through the opening or openings. In this way, it can be reliably ensured that the conductors are electrically insulated from the absorbent core, while the electrodes can be arranged in contact with the absorbent core in a simple and efficient manner.

The wetness detection unit may be configured to detect the wetness at the one or more locations within the absorbent core by measuring the electrical resistance between two of the electrodes through the conductors. The wetness detection unit may be configured to detect the wetness at the one or more locations within the absorbent core by measuring the electrical resistance between adjacent ones of the electrodes, i.e., electrodes which are adjacent to each other, through the conductors.

In particular, if a wetness event occurs in the absorbent core, the electrical conductivity of the portion or portions of the absorbent core at which the event occurs changes, i.e., increases, due to the presence of a fluid, such as urine or other bodily fluids, in the portion or portions. Thus, the electrical resistance between the electrodes, e.g., adjacent ones of the electrodes, in the vicinity of this portion or these portions or at this portion or these portions also changes, i.e., decreases. This change in resistance is measured by the wetness detection unit through the conductors which are electrically connected to the respective electrodes.

The degree, i.e., amount, of the resistance change measured by the wetness detection unit depends on the amount of fluid present in the portion or portions, i.e., on the intensity of the wetness event. Hence, by measuring the degree of the resistance change, the wetness detection unit can determine the level of saturation of the wearable absorbent article, thus allowing for the user or carer to be alerted to saturation or impending saturation of the absorbent article.

Further, by identifying between which of the electrodes a resistance change has occurred, the wetness detection unit can determine the location or locations of the wetness event in the absorbent core. For example, this information can be used for identifying the type of the wetness event, e.g., whether the fluid present in the portion or portions of the absorbent core is urine or feces, and/or for choosing an appropriate type of wearable absorbent article for a particular user.

However, in some embodiments, it is sufficient that only the level of saturation of the wearable absorbent article, or the mere occurrence of a wetting event, is determined by the wetness detection unit.

Each of the electrodes may extend along an extension direction. All of the electrodes may extend along the same extension direction. All of the electrodes may have substantially the same length in the extension direction or the respective extension directions. The extension directions of the electrodes may be substantially perpendicular to the extension directions of the conductors to which they are respectively electrically connected.

The extension direction of a particular electrode is the direction along which the particular electrode extends, i.e., the direction along the length of the particular electrode. The extension direction may be a straight direction but is not restricted thereto. For example, alternatively, the extension direction may be a curved or curvilinear direction, an undulating or wavy direction, an elliptic or circular direction etc.

The extension directions of the electrodes may be substantially parallel to each other. For example, the extension directions of the electrodes may be parallel straight directions, parallel curved or curvilinear directions, parallel undulating or wavy directions, parallel elliptic or circular directions etc. In particular, two or more electrodes may be arranged in concentric circles.

Alternatively, the extension directions of the electrodes may not be parallel to each other.

The extension directions of the electrodes may be substantially perpendicular to a longitudinal centre line of the wearable absorbent article. The longitudinal centre line may extend from a front side of the article, facing a front side of the wearer in use thereof, to a back side of the article, facing a back side of the wearer in use thereof.

The extension directions of the conductors may be substantially parallel to the longitudinal centre line of the wearable absorbent article. In this way, the locations within the absorbent core at which wetness can be detected by the wetness detection unit can be arranged in a staggered or sequential manner along the longitudinal centre line, i.e., so that one location is arranged after the other in the direction of the longitudinal centre line. This arrangement allows for an especially accurate wetness detection, in particular, with regard to the location or locations where the one or more wetness events have occurred.

The extension directions of the conductors may be substantially parallel to each other. For example, the extension directions of the conductors may be parallel straight directions, parallel curved or curvilinear directions, parallel undulating or wavy directions, parallel elliptic or circular directions etc.

Alternatively, the extension directions of the conductors may not be parallel to each other.

The wetness detection unit may be removably attached to the remainder of the absorbent article. In this case, the wetness detection unit can be replaced in a particularly simple and efficient manner, for example, if the detection unit is damaged or has to be recharged or attached to a fresh article for reuse.

As has been detailed above, the wearable absorbent article may include a liquid peitneable inner or top layer adapted to face the wearer during use and adapted to allow a fluid, such as urine or other bodily fluids, to pass through, a liquid impermeable outer or bottom layer adapted to face away from the wearer and adapted to prevent the fluid from passing through, and an absorbent core located between the inner or top layer and the outer or bottom layer. Moreover, optionally, further additional layers may be arranged between the inner or top layer and the outer or bottom layer.

The wearable absorbent article is not limited to employing particular types of absorbent core. Absorbent cores containing any commonly available absorbent material may be used. Such absorbent materials include, but are not limited to, cellulosic fibres, absorbent foams, super absorbent polymers, absorbent gelling materials or any other known absorbent material or combination of materials.

The absorbent core may include one or more layers of absorbent material that may have the same composition and/or shape or may have different compositions and/or shapes.

For example, the wetness detection unit may be removably attached to the outer or bottom layer of the absorbent article. The wetness detection unit may be removably attached to the front side of the article, facing the front side of the wearer in use thereof, or to the back side of the article, facing the back side of the wearer in use thereof. Further, the wetness detection unit may be removably attached to a lateral side of the article.

The wetness detection unit may be embedded within the remainder of the absorbent article. This configuration allows for a particularly secure and simple arrangement of the wetness detection unit.

In particular, the wetness detection unit may be arranged between the inner or top layer and the outer or bottom layer of the absorbent article. In embodiments, the wetness detection unit is arranged between the absorbent core and the outer or bottom layer, or between two layers of absorbent material of the absorbent core.

All of the conductors may have substantially the same electrical resistance, i.e., substantially the same overall or total electrical resistance. In this case, any differences in resistance of the conductors are eliminated, thus allowing for wetness at one or more locations within the absorbent article to be detected with a particularly high degree of accuracy.

The electrical resistance may be defined at a conductor temperature of 20° C.

Those of the at least some of the conductors which have larger lengths in the respective extension directions may have cross-sectional areas perpendicular to the respective extension directions which are larger than the cross-sectional areas perpendicular to the respective extension directions of those of the at least some of the conductors which have smaller lengths in the respective extension directions. In this way, the differences in resistance, i.e., overall or total resistance, of the conductors resulting from their different lengths can be reduced or even eliminated in a particularly simple and efficient manner.

The cross-sectional areas of the conductors perpendicular to the respective extension directions may be proportional to the lengths of the conductors in the respective extension directions. In this way, it can be ensured in a simple manner that there are no differences between the resistances of the conductors, so that wetness at one or more locations within the absorbent article can be detected with a particularly high degree of accuracy.

Suitable materials for the conductors and electrodes include commonly known electrically conductive materials, such as metals, e.g., copper, aluminium, silver or the like, metal alloys, electrically conductive organic compounds, such as electrically conductive polymers, or electrically conductive inorganic compounds, such as conductive oxides.

All of the conductors may be made from the same material. Alternatively, some or all of the conductors may be made from different materials.

The electrodes may be made from the same material as the conductors or from a different material or different materials. All of the electrodes may be made from the same material, or alternatively, some or all of the electrodes may be made from different materials.

Those of the at least some of the conductors which have larger lengths in the respective extension directions may have lower electrical resistivities than those of the at least some of the conductors which have smaller lengths in the respective extension directions. In this way, the differences in resistance, i.e., overall or total resistance, of the conductors resulting from their different lengths can be reduced or even eliminated in a particularly simple and efficient manner.

The electrical resistivity may be defined at a conductor temperature of 20° C.

In particular, those of the at least some of the conductors which have larger lengths in the respective extension directions may be made of materials having lower electrical resistivities than the materials of which those of the at least some of the conductors are made which have smaller lengths in the respective extension directions.

The electrical resistivities of the conductors may be inversely proportional to the lengths of the conductors in the respective extension directions. In this way, it can be ensured in a simple manner that there are no or limited differences between the resistances of the conductors, so that wetness at one or more locations within the absorbent article can be detected with a particularly high degree of accuracy.

The electrical resistivities of the materials of which the conductors are made may be essentially inversely proportional to the lengths of the conductors in the respective extension directions.

In one embodiment, those of the at least some of the conductors which have larger lengths in the respective extension directions have cross-sectional areas perpendicular to the respective extension directions which are larger than the cross-sectional areas perpendicular to the respective extension directions of those of the at least some of the conductors which have smaller lengths in the respective extension directions, and those of the at least some of the conductors which have larger lengths in the respective extension directions have lower electrical resistivities than those of the at least some of the conductors which have smaller lengths in the respective extension directions.

All of the conductors may extend along the same extension direction. This extension direction may be parallel to the longitudinal centre line of the wearable absorbent article.

The conductor arrangement may further include a flexible circuit board.

The flexible circuit board may include the insulating substrate and the insulating layer detailed above. The conductors and the electrodes may be disposed between the insulating substrate and the insulating layer so that the conductors are covered by the insulating layer and the electrodes are exposed through the one or more openings.

The wetness detection unit may be provided on the flexible circuit board.

The flexible circuit board may further include one or more electronic components, such as a power source providing power to the wetness detection unit, one or more detection unit-controlling electronic components, such as a control unit, and/or one or more transmission means, e.g., for transmitting a wetness detection unit reading to an external unit adapted to receive the detection unit signal. The detection unit signal may be transmitted wirelessly or by wired connection.

The conductor arrangement, the electrodes, the wetness detection unit, the power source and the control unit together form a wetness sensor.

The conductors may be strip conductors or strip lines formed on the flexible circuit board.

The conductors may have lengths in the respective extension directions in the range of 1 cm to 60 cm, in the range of 2 cm to 50 cm, or in the range of 4 cm to 40 cm.

The conductors may have cross-sectional areas perpendicular to the respective extension directions in the range of 0.01 mm$^2$ to 1.00 mm$^2$, in the range of 0.02 mm$^2$ to 0.80 mm$^2$, or in the range of 0.05 mm$^2$ to 0.60 mm$^2$.

The conductors may have electrical resistivities at conductor temperatures of 20° C. in the range from $1.0 \times 10^{-8}$ $\Omega$m to $5.0 \times 10^{-8}$ $\Omega$m, in the range from $1.5 \times 10^{-8}$ $\Omega$m to $4.0 \times 10^{-8}$ $\Omega$m or in the range from $2.0 \times 10^{-8}$ $\Omega$m to $3.5 \times 10^{-8}$ $\Omega$m.

BRIEF DESCRIPTION OF THE DRAWINGS

For a better understanding of the present invention and to show how the same may be carried into effect, reference will now be made, by way of example only, to the accompanying drawings, in which:

FIGS. 3A and 3B illustrate a second embodiment of a flexible circuit board comprised in the wearable absorbent article shown in FIG. 1, wherein

DETAILED DESCRIPTION OF PARTICULAR EMBODIMENTS

Figure 1:
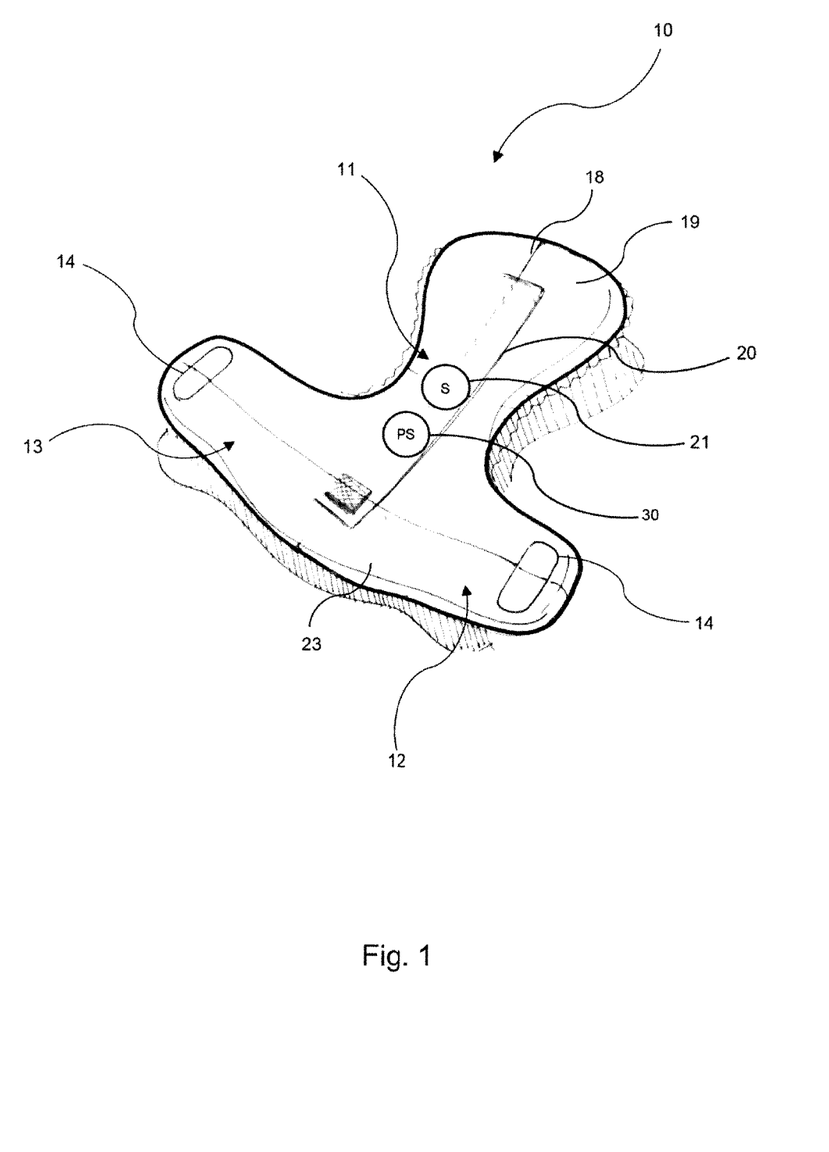
FIG. 1 shows a wearable absorbent article according to an embodiment.

FIG. 1 shows a wearable absorbent article 10.

The wearable absorbent article 10 is a diaper, in particular, a refastenable diaper.

The wearable absorbent article 10 has a main portion 11, a first side portion 12, a second side portion 13 and attachment members 14. The main portion 11 is elongate in a first direction. The first direction is parallel to a longitudinal centre line 18 of the wearable absorbent article 10. The longitudinal centre line 18 extends from a front side 19 of the absorbent article 10, facing a front side of the wearer in use thereof, to a back side 23 of the absorbent article 10, facing a back side of the wearer in use thereof.

The first side portion 12 and the second side portion 13 extend away from the main portion 11 along a second direction perpendicular to the first direction. The first side portion 12 and the second side portion 13 extend away from the main portion 11 on opposite sides of the main portion 11. An attachment member 14 is disposed on both side portions 12, 13.

The wearable absorbent article 10 is configured to be worn around the waist of a user by attaching the side portions 12, 13 to the main portion 11 using the attachment members 14.

Figure 4:
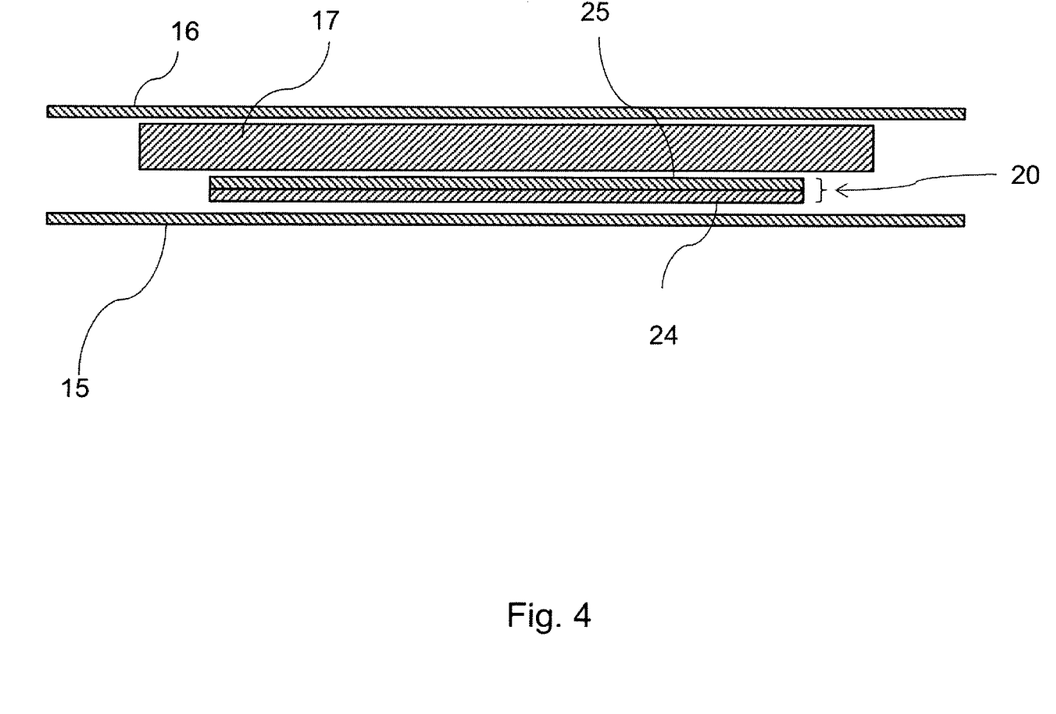
FIG. 4 is a cross-sectional view of the wearable absorbent article shown in FIG. 1 including the flexible circuit board shown in FIG. 2.
Figure 5:
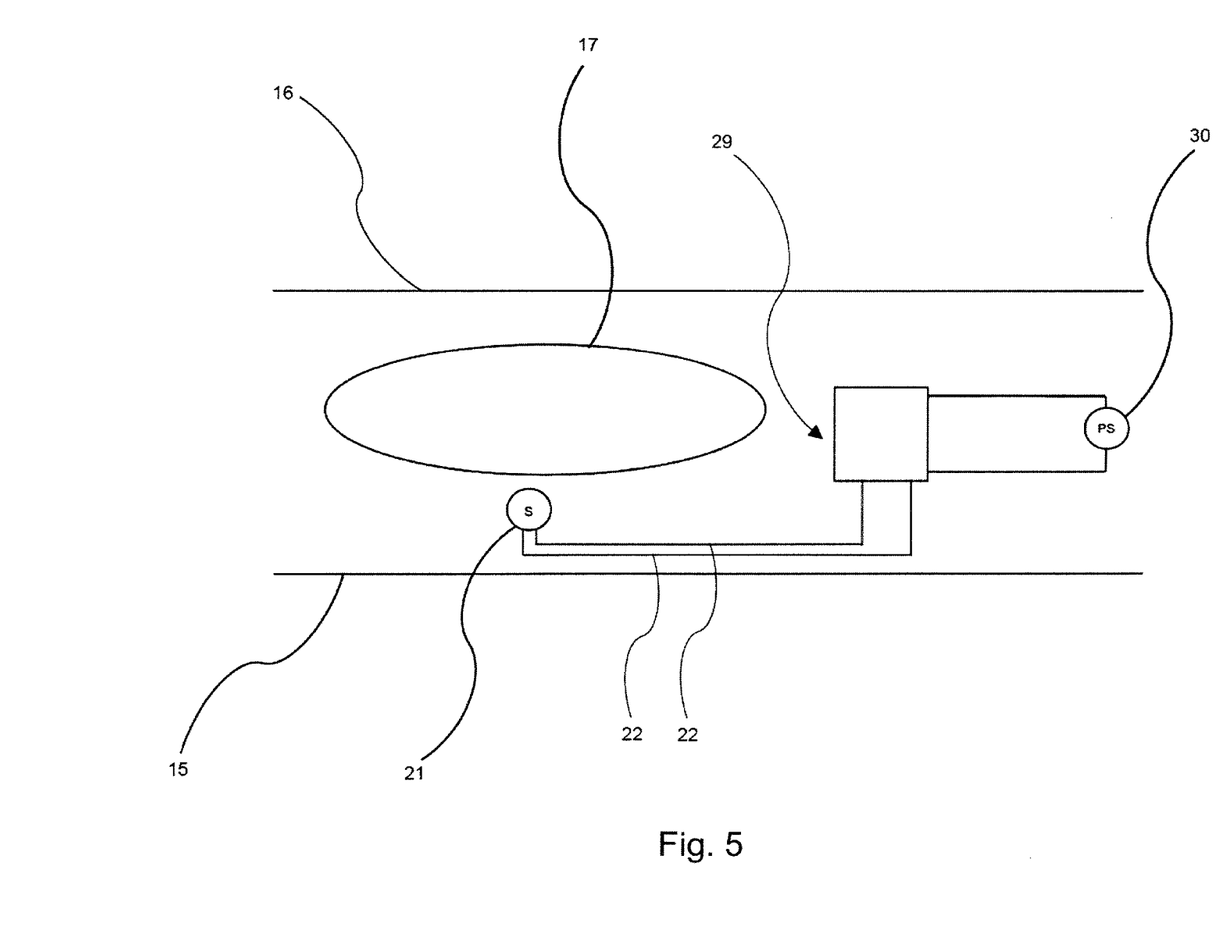
FIGS. 5 and 6 are cross-sectional views, showing two different possible arrangements of a wetness detection unit, a control unit and a power source of the wearable absorbent article shown in FIG. 1.
Figure 6:
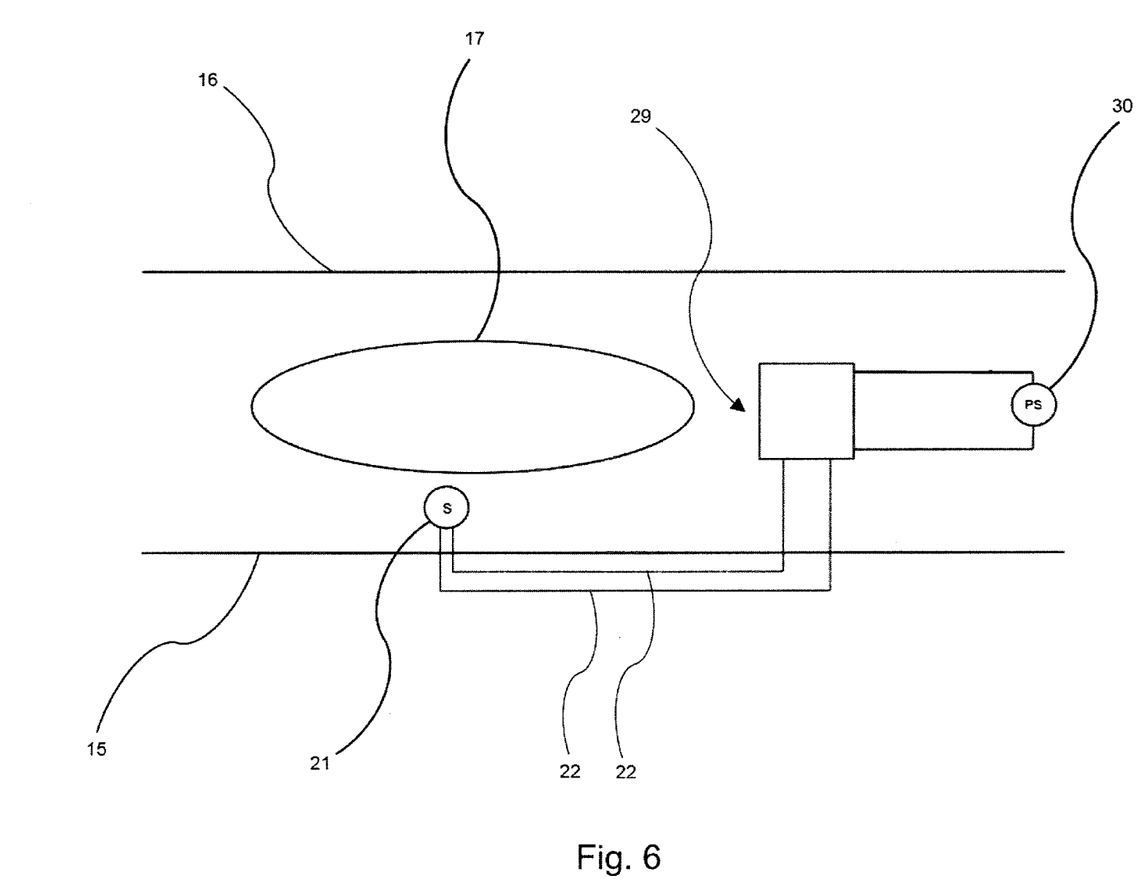

The wearable absorbent article 10 has a liquid permeable top layer adapted to face the wearer during use and adapted to allow a fluid, such as urine or other bodily fluids, to pass through, a liquid impermeable bottom layer adapted to face away from the wearer during use and adapted to prevent the fluid from passing through, and an absorbent core located between the top layer and the bottom layer (see FIGS. 4 to 6).

FIG. 1 shows the wearable absorbent article 10 in an unfolded configuration. This configuration of the wearable absorbent article 10 is typical before the application of the wearable absorbent article 10 to a wearer.

The wearable absorbent article 10 includes a conductor arrangement (see FIGS. 2 to 4) with a flexible circuit board 20. The conductor arrangement includes a plurality of elongate conductors and a plurality of electrodes, each of the electrodes being electrically connected to a respective one of the conductors. The flexible circuit board 20 has attached thereto a wetness detection unit 21, a control unit for controlling the wetness detection unit 21, and a power source 30 providing power to the control unit and the wetness detection unit 21, as will be detailed below with reference to FIGS. 2 to 6.

The flexible circuit board 20 may further have a transmitter for transmitting information relating to the wetness detected by the wetness detection unit 21 or other relevant information. The flexible circuit board 20 may further have a receiver for receiving information, such as instructions.

In FIG. 4, the flexible circuit board 20 is disposed in the main portion 11 of the wearable absorbent article 10, between the absorbent core and the bottom layer.

The power source 30 may hold an energy store in the form of electrical energy and/or a chemical energy. The power source 30 may be any type of power source, such as a cell, a battery and/or a capacitor. For example, the power source 30 may be a flexible paper cell/battery, such as those provided by Blue Spark Technologies (OH, US), Enfucell Oy (FI), GS Nanotech (KR) or Cymbet (MN, US).

Figure 2:
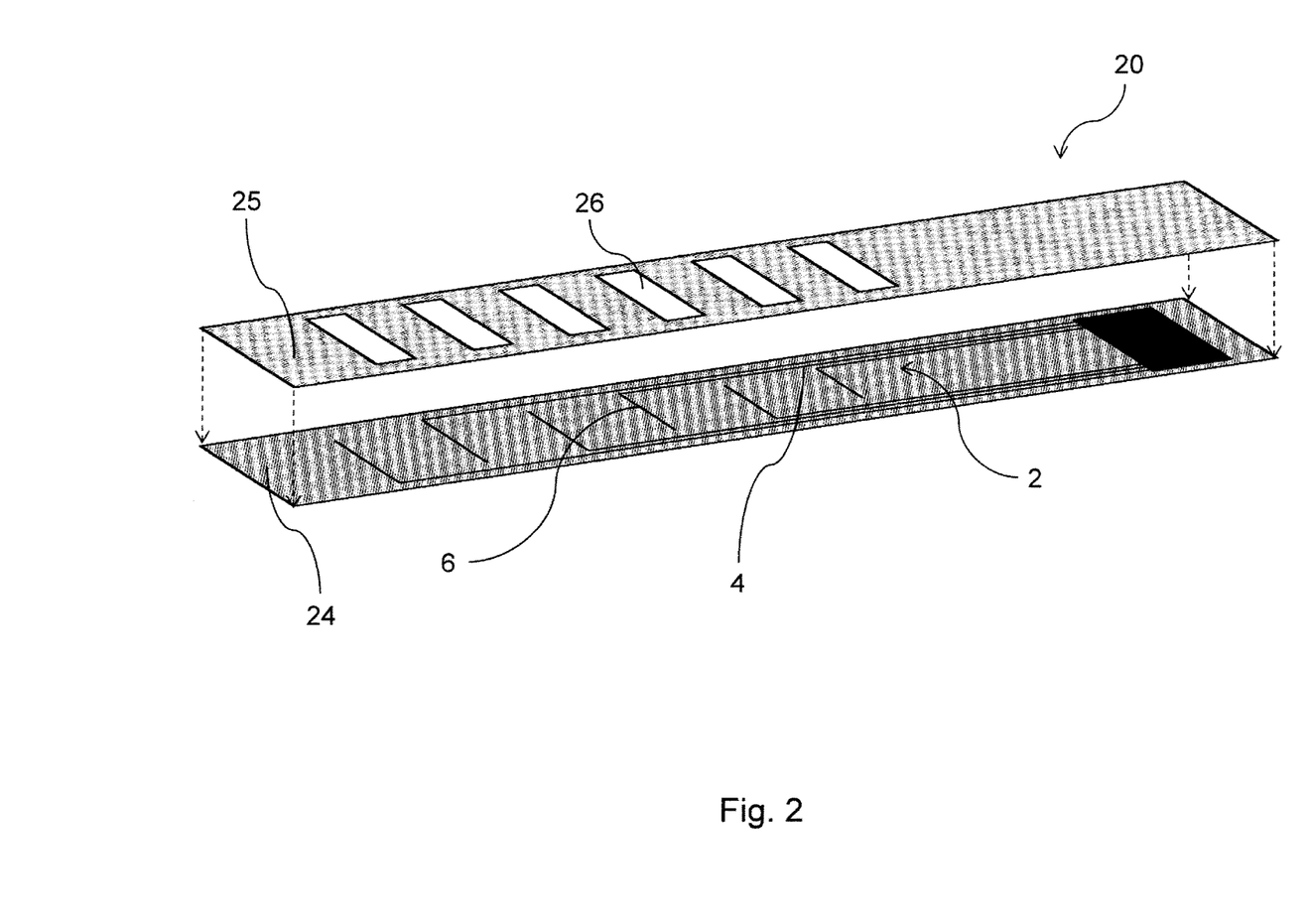
FIG. 2 shows an exploded view of a first embodiment of a flexible circuit board comprised in the wearable absorbent article shown in FIG. 1.

FIG. 2 shows an exploded view of a first embodiment of a flexible circuit board comprised in the wearable absorbent article 10 shown in FIG. 1. FIGS. 3A and 3B illustrate a second embodiment of a flexible circuit board comprised in the wearable absorbent article 10 shown in FIG. 1. These two embodiments substantially only differ from each other in the number of conductors and electrodes, i.e., the flexible circuit board of the first embodiment has six conductors and electrodes, while the flexible circuit board of the second embodiment has nine conductors and electrodes. Hence, the same reference signs are used for the flexible circuit boards of the first and second embodiments and their components. In particular, reference sign 20 denotes the flexible circuit board (see also FIG. 1).

The flexible circuit board 20 includes an insulating substrate 24 and an insulating layer 25 arranged on top of the substrate 24, as is shown in FIG. 2. The insulating layer 25 has a plurality of openings 26.

The insulating substrate 24 and/or the insulating layer 25 may be made of a polymer material, such as, but not limited to polyethylene terephthalate (PET), polyimide (PI), polyethylene naphthalate (PEN), polyetherimide (PEI) or ethylene vinyl acetate (EVA).

The wearable absorbent article 10 includes a conductor arrangement 2. The conductor arrangement 2 includes a plurality of elongate conductors 4, each conductor extending along the same extension direction. In FIG. 1, the extension direction of the conductors 4 is parallel to the longitudinal centre line 18 of the wearable absorbent article 10. The conductors 4 are provided on the insulating substrate 24 of the flexible circuit board 20. In particular, the conductors 4 may be strip conductors or strip lines formed on the insulating substrate 24.

In FIGS. 2 and 3A, all of the conductors 4 have different lengths from each other in the extension direction. Those of the conductors 4 which have larger lengths in the extension direction have lower electrical resistances per unit length than those of the conductors 4 which have smaller lengths in the extension direction.

In particular, as is schematically shown in FIG. 3A, those of the conductors 4 which have larger lengths in the extension direction have cross-sectional areas perpendicular to the extension direction which are larger than the cross-sectional areas perpendicular to the extension direction of those of the conductors 4 which have smaller lengths in the extension direction. In this way, the differences in resistance, i.e., overall or total resistance, of the conductors 4 resulting from their different lengths can be reduced or even eliminated in a particularly simple and efficient manner.

Further, those of the conductors 4 which have larger lengths in the extension direction may be made of materials, e.g., metals and/or metal alloys, having lower electrical resistivities than the materials, e.g., metals and/or metal alloys, of which those of the conductors are made which have smaller lengths in the extension direction.

The cross-sectional areas and/or the materials of the conductors 4 may be chosen such that all of the conductors 4 have substantially the same electrical resistance.

In FIGS. 2 and 3A, each of the conductors 4 of the conductor arrangement 2 is electrically connected to a respective electrode 6. Specifically, each of the electrodes 6 is electrically connected to a respective conductor 4 at the distal end of the conductor 4 in the extension direction thereof, i.e., the end of the conductor 4 which is disposed further away from the wetness detection unit 21.

All of the electrodes 6 extend along the same extension direction. The extension direction of the electrodes 6 is substantially perpendicular to the extension direction of the conductors 4. All of the electrodes 6 have substantially the same length in the extension direction.

In FIG. 2, the conductors 4 and the electrodes 6 are disposed between the insulating substrate 24 and the insulating layer 25 so that the conductors 4 are covered by the insulating layer 25 and the electrodes 6 are exposed through the openings 26. In this way, it can be reliably ensured that the conductors 4 are electrically insulated from the absorbent core of the wearable absorbent article 10 (see FIGS. 4 to 6), while the electrodes 6 can be arranged in contact with the absorbent core in a simple and efficient manner. In this way, upon the occurrence of a wetness event in the absorbent core, an electrical contact is established between a respective one or respective ones of the electrodes 6 and the absorbent core.

The wetness detector 21 is configured to detect the wetness at the one or more locations within the absorbent core by measuring the electrical resistance between adjacent ones of the electrodes 6, i.e., electrodes 6 which are adjacent to each other, through the conductors 4. In particular, this electrical resistance may be measured at electrical contacts 27, each of which is electrically connected to a respective conductor 4 at a proximal end of the conductor 4 in the extension direction thereof, i.e., at the end of the conductor 4 which is disposed closer to the wetness detection unit 21 (see FIGS. 3A and 3B). These electrical contacts 27 are arranged adjacent to each other along the extension direction of the conductors 4, i.e., along the longitudinal centre line 18 of the wearable absorbent article 10.

In FIGS. 2 and 3A, the wetness detection unit 21, the control unit and the power source 30 (see FIGS. 1, 5 and 6) have been omitted for the sake of simplicity. These components will be described in further detail below with reference to FIGS. 5 and 6. Moreover, in FIG. 3A, the insulating layer 25 (see FIG. 2) has been omitted for the sake of simplicity.

FIG. 4 is a cross-sectional view of the wearable absorbent article 10 shown in FIG. 1 including the flexible circuit board 20 shown in FIG. 2. The cross-sectional view of FIG. 4 is taken along a plane perpendicular to the second direction (see FIG. 1). The cross-sectional view is a cross-sectional view of the main portion 11 of the wearable absorbent article 10 (see FIG. 1).

In FIG. 4, the wetness detection unit 21, the control unit and the power source 30 (see FIGS. 1, 5 and 6) have been omitted for the sake of simplicity.

The wearable absorbent article 10 shown in FIG. 4 has a liquid permeable top layer 16 adapted to face the wearer during use and to allow a fluid, such as urine or other bodily fluids, to pass through, a liquid impermeable bottom layer 15 opposite to the top layer 16, which is adapted to prevent the fluid from passing through, and an absorbent core 17 located between the bottom layer 15 and the top layer 16 for absorbing the fluid.

As is shown in FIG. 4, the flexible circuit board 20, including the insulating substrate 24 and the insulating layer 25, is arranged between the absorbent core 17 and the bottom layer 15. In particular, the flexible circuit board 20 is disposed so that the insulating substrate 24 faces the bottom layer 15 and the insulating layer 25 faces the absorbent core 17.

Figure 3:
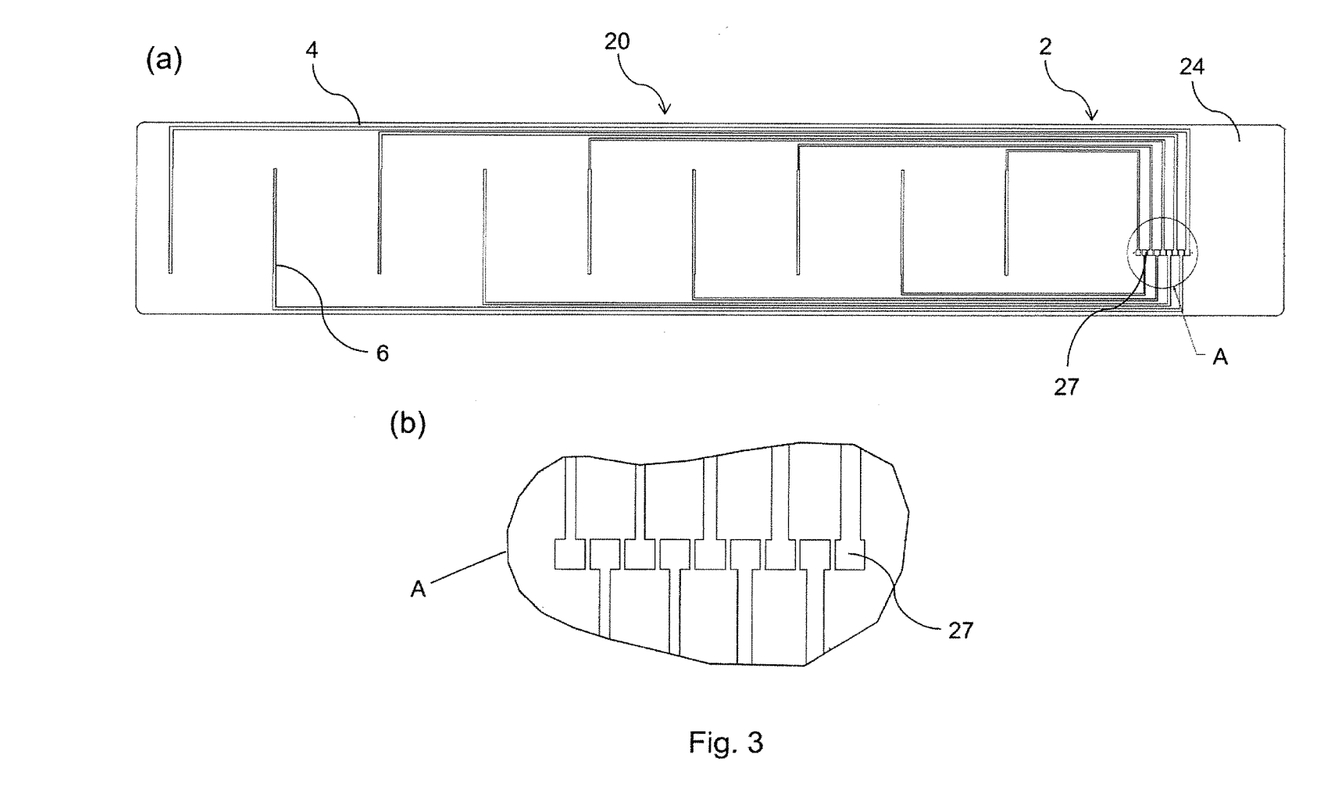
FIG. 3A shows a top view of a portion of the flexible circuit board.
FIG. 3B shows an enlarged view of the region A in FIG. 3A.

Further, in FIGS. 2 and 3, the flexible circuit board 20 is arranged so that the electrodes 6 are in contact with the absorbent core 17, while the conductors 4 are electrically insulated from the absorbent core 17 by the insulating layer 25, as has been detailed above. Upon the occurrence of a wetness event in the absorbent core 17, an electrical contact is established between respective ones of the electrodes 6 and the absorbent core 17. In this way, an electrical contact is established between at least two of the electrodes 6 through the absorbent core 17.

The wetness detection unit 21 (not shown in FIG. 4) is configured to detect the wetness at the one or more locations within the absorbent core 17 by measuring the electrical resistance between at least two, e.g., adjacent ones, of the electrodes 6 through the conductors 4. The electrical resistance may be measured at the electrical contacts 27 (see FIGS. 3A and 3B), as has been detailed above. The wetness measurement performed by the wetness detection unit 21 will be explained in more detail below with reference to FIGS. 5 and 6.

FIGS. 5 and 6 are cross-sectional views, taken along a plane perpendicular to the second direction (see FIG. 1) and showing two different possible arrangements of the wetness detection unit 21, the control unit 29 and the power source 30 of the wearable absorbent article 10 shown in FIG. 1. In particular, the cross-sectional views shown in these drawings are cross-sectional views of the main portion 11 of the wearable absorbent article 10 (see FIG. 1).

The conductor arrangement 2, the electrodes 6, the wetness detection unit 21, the power source 30 and the control unit 29 together form a wetness sensor.

In FIGS. 5 and 6, the flexible circuit board 20, the conductors 4 and the electrodes 6 (see FIGS. 2 and 3) have been omitted for the sake of simplicity.

The general configuration of the wearable absorbent articles 10 shown in FIGS. 5 and 6 is substantially the same as that of the wearable absorbent article 10 shown in FIG. 4. Hence, the same reference signs have been used to denote identical or substantially identical components thereof.

In particular, in each of the different arrangements shown in FIGS. 5 and 6, the wearable absorbent article 10 has the liquid permeable top layer 16 adapted to face the wearer during use and to allow a fluid, such as urine or other bodily fluids, to pass through, the liquid impermeable bottom layer 15 opposite to the top layer 16, which is adapted to prevent the fluid from passing through, and the absorbent core 17 located between the bottom layer 15 and the top layer 16 for absorbing the fluid.

The flexible circuit board 20 (not shown in FIGS. 5 and 6) is arranged so that the electrodes 6 (see FIGS. 2 and 3) are in contact with the absorbent core 17, while the conductors 4 are electrically insulated from the absorbent core 17 by the insulating layer 25, as has been detailed above. Upon the occurrence of a wetness event in the absorbent core 17, an electrical contact is established between respective ones of the electrodes 6 and the absorbent core 17. In this way, an electrical contact is established between at least two of the electrodes 6 through the absorbent core 17.

The wetness detection unit 21 is configured to detect the wetness at the one or more locations within the absorbent core 17 by measuring the electrical resistance between at least two, e.g., adjacent ones, of the electrodes 6 through the conductors 4. The electrical resistance is measured at the electrical contacts 27 (see FIGS. 3A(a) and 3B(b)), as has been detailed above.

If a wetness event occurs in the absorbent core 17, the electrical conductivity of the portion or portions of the absorbent core 17 at which the event occurs increases due to the presence of a fluid, such as urine or other bodily fluids, in the portion or portions. Thus, the electrical resistance between at least two, e.g., adjacent ones, of the electrodes 6 in the vicinity of this portion or these portions or at this portion or these portions decreases. This change in resistance is measured by the wetness detection unit 21 through the conductors 4 which are electrically connected to the respective electrodes 6.

The degree of the resistance change measured by the wetness detection unit 21 depends on the amount of fluid present in the portion or portions, i.e., on the intensity of the wetness event. Therefore, by measuring the degree of the resistance change, the wetness detection unit 21 can determine the level of saturation of the wearable absorbent article 10, i.e., of the absorbent core 17, so that the user or carer can be alerted to saturation or impending saturation of the absorbent article 10.

Further, by identifying between which of the electrodes 6 a resistance change has occurred, the wetness detection unit 21 can determine the location or locations of the wetness event in the absorbent core 17. This information can be used for identifying the type of the wetness event, e.g., whether the fluid present in the portion or portions of the absorbent core 17 is urine or feces, and/or for choosing an appropriate type of wearable absorbent article 10 for a particular user.

The control unit 29 is configured to control the wetness detection unit 21. The control unit 29 may be configured to process the data measured by the wetness detection unit 21. The control unit 29 may be any type of control, such as, for example, a microprocessor.

In FIGS. 5 and 6, the control unit 29 is electrically connected to the wetness detection unit 21 by a pair of leads 22. The control unit 29 is arranged at a location distant from the flexible circuit board 20.

The power source 30 provides power to the control unit 29 and the wetness detection unit 21. The power source 30 may be any type of power source, such as a cell, a battery and/or a capacitor, as has been detailed above.

FIG. 5 shows an arrangement in which the wetness detection unit 21, the leads 22, the control unit 29 and the power source 30 are arranged between the bottom layer 15 and the top layer 16 of the wearable absorbent article 10. In particular, the wetness detection unit 21 is disposed between the absorbent core 17 and the bottom layer 15.

The wetness detection unit 21 is thus embedded within the remainder of the wearable absorbent article 10. This configuration allows for a particularly simple and secure arrangement of the wetness detection unit 21. In particular, the wetness detection unit 21 is safely protected from any external influences by the bottom layer 15 and the top layer 16 of the wearable absorbent article 10.

FIG. 6 shows an alternative arrangement which differs from the arrangement shown in FIG. 5 only in that the leads 22 are not disposed between the bottom layer 15 and the top layer 16. As is shown in FIG. 6, the leads 22 are provided on an outer side of the bottom layer 15. This configuration enables particularly easy access to the leads 22, for example, in the case of any damage thereto.

In another alternative arrangement, the wetness detection unit 21 may not be disposed between the bottom layer 15 and the top layer 16. In particular, the wetness detection unit 21 may be provided on an outer side of the bottom layer 15.

The wetness detection unit 21 may be removably attached to the outer side of the bottom layer 15. In this case, the wetness detection unit 21 can be replaced in a particularly simple and efficient manner, for example, if the wetness detection unit 21 is damaged. Moreover, the wetness detection unit 21 can be reused for other wearable absorbent articles in a simple way.

In further alternative arrangements, the control unit 29 and/or the power source 30 may not be disposed between the bottom layer 15 and the top layer 16 of the wearable absorbent article 10.

All of the above are fully within the scope of the present invention, and are considered to form the basis for alternative embodiments in which one or more combinations of the above-described features are applied, without limitation to the specific combinations disclosed above.

In light of this, there will be many alternatives which implement the teaching of the present invention. It is expected that one skilled in the art will be able to modify and adapt the above disclosure to suit its own circumstances and requirements within the scope of the present invention, while retaining some or all technical effects of the same, either disclosed or derivable from the above, in light of this common general knowledge in this art. All such equivalents, modifications or adaptations fall within the scope of the invention hereby defined and claimed.

The invention claimed is:

1. A wearable absorbent article comprising:
   a conductor arrangement comprising a plurality of elongate conductors, each conductor extending along an extension direction, wherein at least some of the conductors (4) have different lengths from each other in the respective extension directions, and wherein those of the at least some of the conductors which have larger lengths in the respective extension directions have lower electrical resistances per unit length than those of the at least some of the conductors (4) which have smaller lengths in the respective extension directions;
   an absorbent core; and
   a wetness detection unit for detecting wetness at one or more locations within the absorbent core,
   wherein the conductors are arranged so as to be electrically insulated from the absorbent core,
   wherein each of the conductors is electrically connected to a respective electrode, the electrodes are arranged in contact with the absorbent core, and the wetness detection unit is configured to detect the wetness at the one or more locations within the absorbent core by measuring the electrical resistance between two of the electrodes through the conductors.

2. The wearable absorbent article according to claim 1, wherein the wetness detection unit is removably attached to the remainder of the absorbent article.

3. The wearable absorbent article according to claim 1, wherein the wetness detection unit is embedded within the remainder of the absorbent article.

4. The wearable absorbent article according to claim 1, wherein all of the conductors have substantially the same electrical resistance.

5. The wearable absorbent article according to claim 1, wherein those of the at least some of the conductors which have larger lengths in the respective extension directions have cross-sectional areas perpendicular to the respective extension directions which are larger than the cross-sectional areas perpendicular to the respective extension directions of those of the at least some of the conductors which have smaller lengths in the respective extension directions.

6. The wearable absorbent article according to claim 5, wherein the cross-sectional areas of the conductors perpendicular to the respective extension directions are substantially proportional to the lengths of the conductors in the respective extension directions.

7. The wearable absorbent article according to claim 1, wherein those of the at least some of the conductors which have larger lengths in the respective extension directions resistivities than those of the have lower electrical at least some of the conductors which have smaller lengths in the respective extension directions.

8. The wearable absorbent article according to claim 7, wherein the electrical resistivities of the conductors are inversely proportional to the lengths of the conductors in the respective extension directions.

9. The wearable absorbent article according to claim 1, wherein all of the conductors extend along the same extension direction.

10. The wearable absorbent article according to claim 1, wherein the conductor arrangement further comprises a flexible circuit board.

11. The wearable absorbent article according to claim 10, wherein the conductors are strip conductors formed on the flexible circuit board.

12. The wearable absorbent article according to claim 1, wherein the conductors have at least one of lengths in the respective extension directions in the range of 1 cm to 60 cm or cross-sectional areas perpendicular to the respective extension directions in the range of 0.01 mm$^2$ to 1.00 mm$^2$.

13. The wearable absorbent article according to claim 1, wherein the absorbent article is a diaper, a sanitary towel, an incontinence garment or a medical dressing.

* * * * *